(12) United States Patent
Suzuki et al.

(10) Patent No.: US 6,318,892 B1
(45) Date of Patent: Nov. 20, 2001

(54) RADIOGRAPHY APPARATUS WITH ROTATABLY SUPPORTED CYLINDRICAL RING CARRYING IMAGE PICKUP UNIT

(75) Inventors: Tsutomu Suzuki, Abiko; Takaaki Kobiki, Noda; Hiroshi Takagi, Kashiwa; Nobuhiko Matsui, Tokyo, all of (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/425,300

(22) Filed: Oct. 25, 1999

(30) Foreign Application Priority Data

Oct. 28, 1998 (JP) ............................................... H10-306238

(51) Int. Cl.$^7$ ........................................................ H05G 1/02
(52) U.S. Cl. .............................. 378/197; 378/193; 378/4; 250/522.1
(58) Field of Search ................................... 378/197, 193, 378/4, 11; 250/522.1

(56) References Cited

U.S. PATENT DOCUMENTS 5,960,054 * 9/1999 Freeman et al. .......................... 378/4
6,031,888 * 2/2000 Ivan et al. ............................... 378/20

* cited by examiner

Primary Examiner—Robert H. Kim
Assistant Examiner—Pamela R. Hobden
(74) Attorney, Agent, or Firm—Antonelli, Terry, Stout & Kraus, LLP

(57) ABSTRACT

A radiography apparatus is constituted by an image pickup unit including an X-ray source for irradiating cone shaped X-ray beams to a patient under examination and an image receptor disposed opposite the x-ray source for receiving x-ray image data of the patient by the irradiated cone shaped x-ray beam; a cylindrical ring which carries the image pickup unit, defines a sufficient space to receive the patient therein so as to permit relative positional change of the patient with respect to the image pickup unit and is supported so as to permit rotation around its center axis; a second arm, an image pickup unit; a first video image processing unit; a second video image processing unit; and a change-over device which changes-over the x-ray image data obtained from the image pickup unit either to the first video image processing unit or to the second video image processing unit, whereby a three-dimensional x-ray image of the patient is obtained depending on necessity during an IVR while temporarily resting or interrupting the IVR.

13 Claims, 5 Drawing Sheets

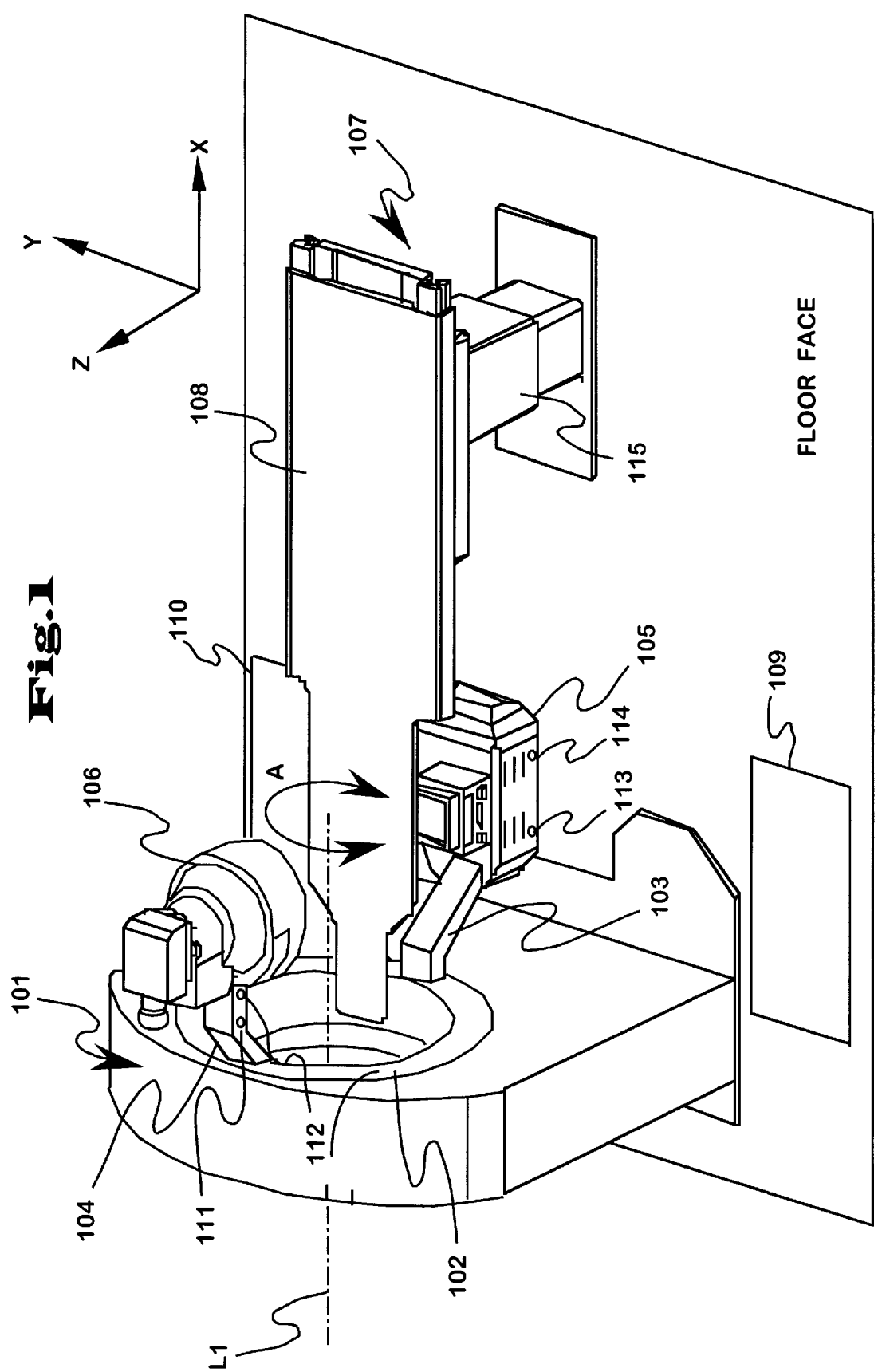

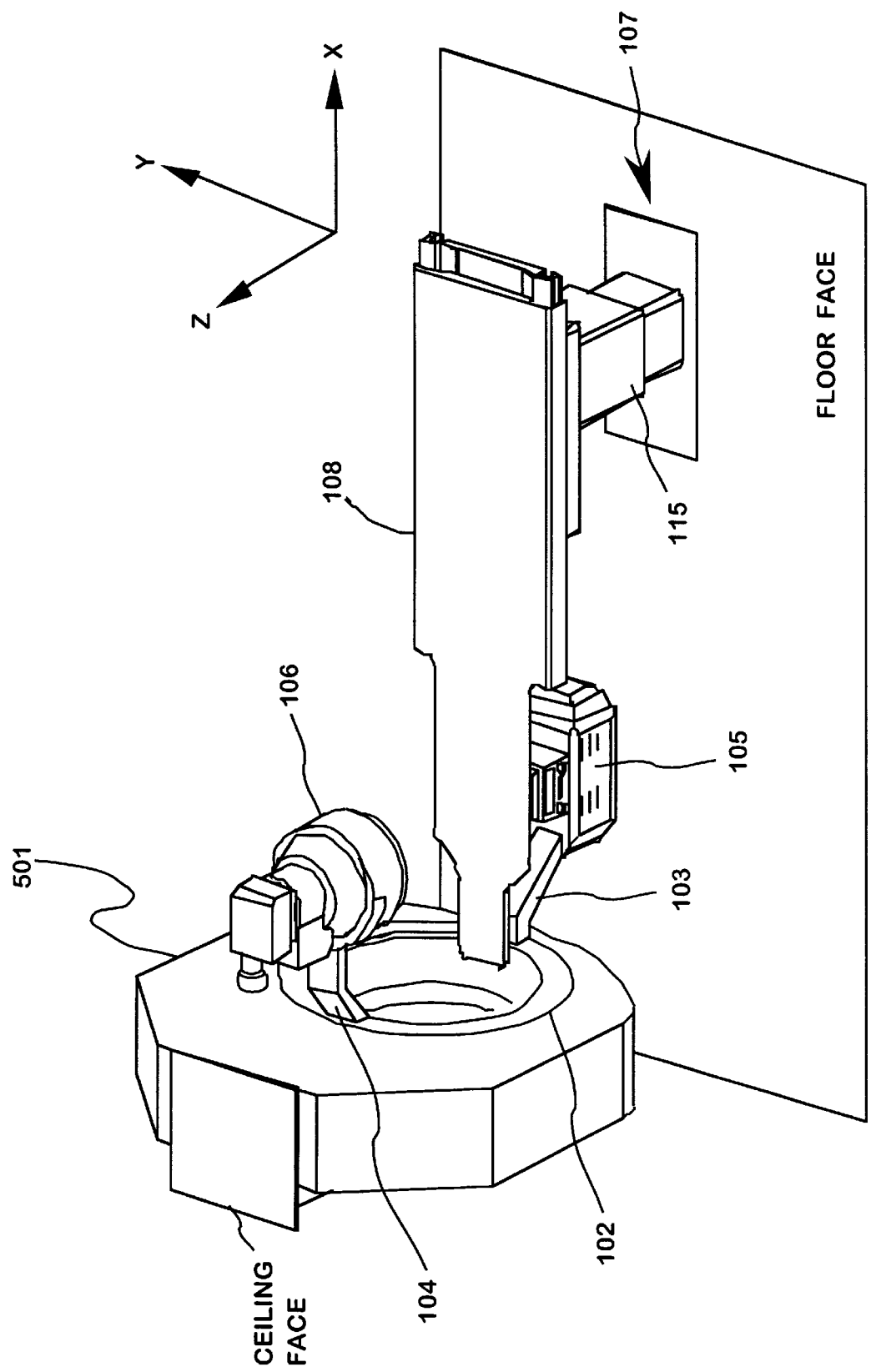

RADIOGRAPHY APPARATUS WITH ROTATABLY SUPPORTED CYLINDRICAL RING CARRYING IMAGE PICKUP UNIT

BACKGROUND OF THE INVENTION

1. Field of the Invention

The present invention relates to a radiography apparatus suitable for a medical treatment called as an IVR (Interventional Radiology, an operation with a catheter under radioscopy observation) using such as an angiographic inspection apparatus and an X ray diagnosis apparatus, and in particular to a radiography apparatus suitable for an X ray inspection and/or diagnosis apparatus for circulatory organs.

2. Conventional Art

In an IVR, an operation is performed by inserting a catheter, at the top of which a variety of treatment tools are attached, into such as blood vessels and internal organs of a patient under radioscopy observation so that even for a medical treatment which conventionally required a laparotomy operation a medical treatment with no laparotomy operation can be performed through an IVR, therefore, such medical treatment is rapidly spreading these days.

During an IVR, a physician under examination and/or operation confirms such as a relative position and a shape of a portion for the treatment object with a three dimensional like X ray image prior to performing a medical operation, and thereafter performs the VIR while confirming the position of a treatment tool attached at the top of the catheter by making use with the two dimensional radioscopic images thereof.

Conventionally, such IVR was performed by making use of a radiography apparatus called as a rotary stereoscope radiography apparatus which uses an X ray source irradiating X rays in a cone shaped beam and an image receptor including an X ray image intensifier (hereinafter called as X ray I.I.) and a television camera, and can produce both two dimensional X ray images and three dimensional like X ray images, and for example, is disclosed in JP-A-6-327663 (1994). In such rotary stereoscope radiography apparatus it is necessary to position a patient in a hollow portion defined in a gantry of a large volume, therefore, a physician is restricted to access the patient in many directions and a work space for the physician is limited which is required for performing a smooth medical treatment for the patient. Further, during an IVR, it is necessary to observe states of the patient such as an outlook in order to quickly respond to a sudden condition change of the patient, however, during an IVR such as for the head of a patient, in particular under a condition that the patient is positioned in the hollow portion defined in the large volume gantry, a visual field of the physician is obstructed by the large volume gantry, therefore, it was difficult to observe the states of the patient such as an outlook thereof, and the physician can not necessarily respond quickly to such as a sudden condition change of the patient.

SUMMARY OF THE INVENTION

An object of the present invention is to provide a radiography apparatus having a large work space for a physician which allows to produce a three dimensional like X ray image during an IVR depending on necessity thereof.

Another object of the present invention is to provide a radiography apparatus having a large work space for a physician which allows to produce a three dimensional like X ray image during an IVR while temporarily resting or interrupting the IVR depending on necessity thereof.

Still another object of the present invention is to provide a radiography apparatus which less obstructs an observation by a physician of a state of a patient such as an outlook thereof, and thus allows the physician to quickly respond to a sudden condition change of the patient.

A further object of the present invention is to provide a radiography apparatus which includes measures to prevent hitting to an obstacle and improves safety of a physician when producing X ray images of the patient from the entire circumferential directions thereof.

A still further object of the present invention is to provide a radiography apparatus which can be installed even in a narrow installation area.

The above and other objects and features of the present invention will become apparent when read the following description of the present invention with reference to the drawings thereof.

One aspect of the present invention is to constitute the radiography apparatus by an image pickup unit including an X ray source for irradiating cone shaped X ray beam to a patient and an image receptor disposed opposite the X ray source for receiving X ray image data of the patient by the irradiated cone shaped X ray beam; a cylindrical ring which carries the image pickup unit, defines a sufficient space to receive the patient therein so as to permit relative positional change of the patient with respect to the image pickup unit and is supported so as to permit rotation around its center axis; a first arm which extends from the cylindrical ring along its center axis and supports the X ray source in the image pickup unit; a second arm which extends from the cylindrical ring along its center axis so as to oppose the first arm and supports the image receptor in the image pickup unit; an image pickup unit rotating mechanism which causes to rotate the cylindrical ring at least one rotation so as to permit rotation of the image pickup unit one time around the patient; a first video image processing unit which produces a radioscopic video image based on the X ray image data obtained from the image pickup unit; a second video image processing unit which reconstructs a three dimensional like video image based on the X ray image data obtained from the image pickup unit; and a change-over switch which changes-over the X ray image data obtained from the image pickup unit either to the first video image processing unit or to the second video image processing unit.

Another aspect of the present invention is to constitute the radiography apparatus by an image pickup unit including an X ray source for irradiating cone shaped X ray beam to a patient and an image receptor disposed opposite the X ray source for receiving X ray image data of the patient by the irradiated cone shaped X ray beam; a supporting member which carries the image pickup unit; a rotary member which carries the supporting member, defines a sufficient space to receive the patient therein so as to permit relative positional change of the patient with respect to the image pickup unit and is supported so as to permit rotation around its center axis; an image pickup unit rotating mechanism which causes to rotate the rotary member at least one rotation so as to permit rotation of the image pickup unit one time around the patient; a video image processing and control unit which processes and controls the X ray image data obtained from the image pickup unit; and an external member which covers the rotary member and the image pickup unit rotating mechanism other than the image pickup unit and the supporting member carrying the image pickup unit, whereby the image pickup unit and the supporting member carrying the image pickup unit are exposed outside the external covering member.

Still another aspect of the present invention is to constitute the radiography apparatus to include an obstacle detection means which is mounted either on the image pickup unit or on the supporting member and detects existence and non-existence of an obstacle on a floor in a rotation range of the image pickup unit, and a rotary member or a cylindrical ring rotation control unit which controls the rotation of the rotary member or the cylindrical ring by the image pickup unit rotating mechanism based on the obstacle detection result by the obstacle detection means.

According to the present invention, since a space is defined at the portion of rotation center of the rotary member or the cylindrical ring supporting the image pickup unit so as to permit relative movement of the patient with respect to the rotary member or the cylindrical ring, thereby either through horizontal movement of the patient in parallel along the rotation center axis or through horizontal movement of the rotary member or the cylindrical ring, the image pickup range of the image pickup unit can be moved from the head of the patient to the foot thereof, thereby any X ray image data can be taken at any horizontal positions of the patient and from entire circumferential directions of the patient without increasing the diameter of the supporting member carrying the image pickup unit, and the three dimensional video image processing unit produces three dimensional like X ray images through a well known reconstruction processing based on the X ray image data taken from the entire directions of the patient to obtain a three dimensional like X ray image of a concerned portion of the patient, thereby, if desired a three dimensional like X ray image of a concerned portion of the patient can be obtained, for example during an IVR, without moving the patient.

Further, according to the present invention since the X ray source and the X ray image receptor are carried by the supporting member having a simple structure which is exposed from the external covering member covering the rotary member or the cylindrical ring supporting the supporting member, the visual field of the physician is less obstructed so that the physician can easily observe the patient and can respond quickly to a sudden condition change of the patient.

Still further, according to the present invention, since the X ray source and the X ray image receptor can be rotated around the patient at any horizontal position of the patient to take X ray image data from entire circumferential directions of the patient without increasing the diameter of the supporting member carrying the X ray source and the X ray image receptor, the safety of the physician can be improved. Further, since it is not required to increase the diameter of the supporting member, the size of the radiography apparatus as a whole can be reduced, thereby, the apparatus can be installed in a narrow installation area.

Moreover, according to the present invention, since the obstacle detection means mounted either on the image pickup unit or on the supporting member is provided which detects a possible obstacle locating in the rotating range of the image pickup unit, and the rotary member or cylindrical ring rotation control unit controls the rotation of the image pickup unit by the image pickup unit rotating mechanism so as to prevent hitting of the image pickup unit to an obstacle, the safety of the apparatus is also improved.

BRIEF DESCRIPTION OF THE DRAWINGS

FIG. 1 is a perspective view of one embodiment of a radiography apparatus according to the present invention;

FIG. 5 is a perspective view of another embodiment of a radiography apparatus according to the present invention.

DETAILED DESCRIPTION OF THE EMBODIMENTS

Figure 2B:
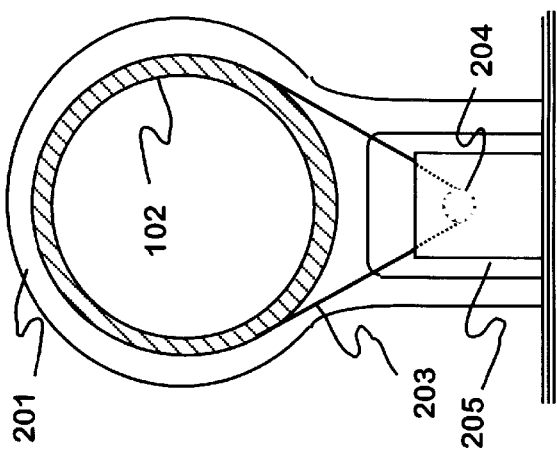
FIG. 2B is a cross sectional view taken along the line IIB—IIB in FIG. 2A

Hereinbelow, embodiments of the present invention are explained with reference to the drawings in which elements having the same functions are designated by the same reference numbers, throughout the drawings and their repeating explanation is saved.

FIG. 1 is a perspective view for explaining an outline structure of a radiography apparatus representing one embodiment according to the present invention, wherein 101 is a stand for an image pickup unit supporting and rotating mechanism, 102 a cylindrical rotating ring, 103 a first arm, 104 a second arm, 105 an X ray tube or X ray source, 106 an X ray detector or image receptor, 107 a table device, 108 a top board, 109 and 110 are mat switches, 111, 112, 113 and 114 are obstacle detection sensors, 115 an elevated portion for the table device 107. X, Y and Z show respectively X, Y and Z axes in the space in which the radiography apparatus is installed. Further, in the present embodiment a supporting member for the image pickup unit including the X ray tube 105 and the X ray detector 106 is constituted by the first arm 103, the second arm 104 and the cylindrical rotating ring 102.

In FIG. 1, the stand 101 is provided with a rotating mechanism which causes to rotate the cylindrical rotating ring 102 along its configuration, and is mounted on the floor face in an upright manner.

The cylindrical rotating ring 102 has a large opening space around the rotation center axis L1 and is provided with the first and second arms 103 and 104 at the side of the table device 107.

At one end of the first arm 103 the X ray tube 105 is disposed and the other end thereof is secured to the cylindrical rotating ring 102, and the first arm 103 supports the X ray tube 105 so that the center of the X rays irradiated from the X ray tube 105 passes through the rotation center axis L1 and makes incident into the X ray detector 106.

At one end of the second arm 104 the X ray detector 106 is disposed and the other end thereof is secured to the cylindrical rotating ring 102, and the second arm 104 supports the X ray detector 106 so that the X ray detector 106 opposes to the X ray tube 105 via the rotation center axis L1.

The X ray tube 105 is a well known X ray tube unit which generates X rays and irradiates the X rays in a radial shape, in a cone shape or in a pyramid shape to a patient under examination and/or operation (not shown), and is disposed at a position opposing to the X ray detector 106 via the not shown patient laid on the top board 108 of the device 107.

The X ray detector 106 is a well known X ray detector which is constituted by a well known I.I. (X ray Image Intensifier), an optical lens system and a television camera, detects X rays for producing two dimensional X ray images which have passed through the not shown patient laid on the top board 108 and converts the same into electrical signals. Although in the present embodiment the X ray detector 106 including the X ray I.I., the optical lens system and the television camera is used, such as flat panel shaped two dimensional X ray detector employing well known TFT elements can be used instead of the above.

The table device 107 is also a well known table device which elevates or deelevates the top band 108 so as set the height of the patient at the center height of the image pickup unit, in other words moves the patient in Z axis direction in FIG. 1, and moves the patient in horizontal direction or X axis direction so as to transfer the patient toward the image taking area defined by the image pickup unit. In the present embodiment the top board 108 is supported so that the longitudinal direction thereof coincides with the direction of the rotation center axis L1. Further, in the present embodiment the top board 108 is supported in a cantilever manner so as not to disturb the rotation of the image pickup unit from the elevation portion 115 of the table device 107.

The mat switches 109 and 110 are well known switches which generate an output based on a pressure applied on the upper surface thereof. In the present embodiment, the mat switches 109 and 110 are a safety measure so as to ascertain that no one such as a physician under examination and/or operation is in the rotating area of the image pickup unit, when the image pickup unit is rotated around the patient in 360°.

An optical sensor, an electrostatic capacitance sensor or a ultrasonic sensor is generally used for the obstacle detection sensors 111, 112, 113 and 114. In the present embodiment, electrostatic capacitance sensors are suitable for the obstacle sensors, because an electrostatic capacitance sensor shows a stable detection performance and can detect a variety of materials possibly operating as obstacles. The electrostatic capacitance sensor is a well known electrostatic capacitance sensor which includes an electrode therein and detects an electrostatic capacitance formed between the electrode and an obstacle, and in the present embodiment the obstacle detection sensors are designed to detect existence and non-existence of an obstacle in the rotating range or area of the X ray tube 105 and the X ray detector 106.

As will be seen from FIG. 1, the radiography apparatus according to the present embodiment is provided with the cylindrical rotating ring 102 which is rotatably supported by a rotating mechanism incorporated in the stand 101 mounted on the floor face in an upright manner. At the side portion of the cylindrical rotating ring 102, in other words at the side in X axis direction, the first arm 103 and the second arm 104 are provided so as to oppose each other in symmetric manner with respect to the rotation center axis L1 of the cylindrical rotating ring 102. At one end of the first arm 103 which extends from the cylindrical rotating ring 102 the X ray tube 105 is mounted, on the other hand, at one end of the second arm 104 which also extends from the cylindrical rotating ring 102 the X ray detector 106 is mounted so as to oppose the X ray tube 105. The table device 107 is structured in such a manner that the elevation portion 115 which supports the top board 108 in a cantilever manner is disposed at a possible most remote position from the stand 101 in X axis direction, the height of the patient can be set at the center height of the image pickup unit and the patient can be moved horizontally from the head side thereof into the X ray image taking area. At such instance the head of the patient may enter into the cylindrical rotating ring 102 depending on the image taking area of the patient, however, according to the radiography apparatus of the present embodiment the cylindrical rotating ring 102 simply supports the X ray tube 105 and X ray detector 106 so as to permit rotation thereof so that the length in X axis direction, in other words depth of the cylindrical rotating ring 102 is shortened. Further, the X ray tube 105 and the X ray detector 106 are carried respectively by the first and second arms 103 and 104 constituting a supporting member in such a manner that both the X ray tube 105 and the X ray detector 106 are projected outside from an external cover for the cylindrical rotating ring 102, therefore, even when the head portion of the patient is entered into the portion of the cylindrical rotating ring 102, the state of the patient such as an outlook thereof can be easily observed so as to permit the physician to quickly respond to a sudden change of the patient according to the radiography apparatus of the present embodiment.

Further, letter A with arrows in FIG. 1 indicates a manner of rotation of the image pickup unit.

Figure 2A:
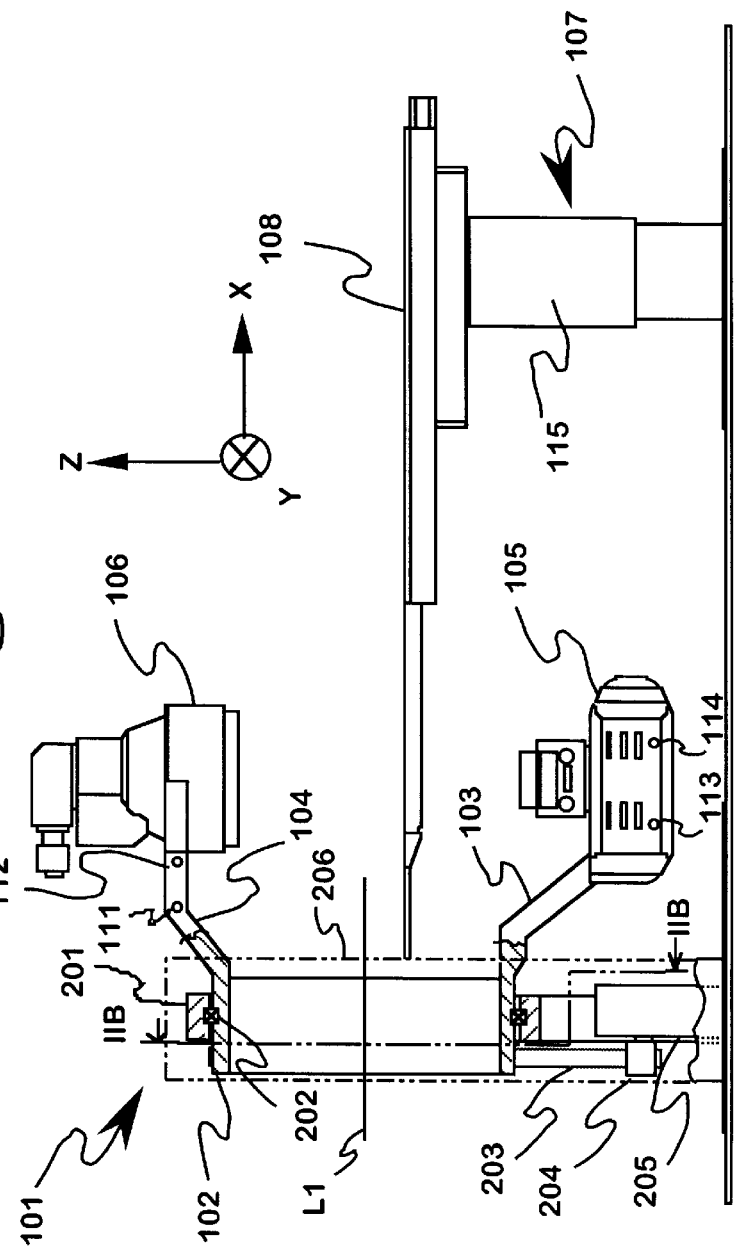
FIG. 2A is a cross sectional view of the radiography apparatus shown in FIG. 1.

FIGS. 2A and 2B are views for explaining a schematic structure of the rotating mechanism for the image pickup unit of the present embodiment as shown in FIG. 1, wherein FIG. 2A is a view for explaining a cross sectional structure of the rotating mechanism for the image pickup unit of the present embodiment and FIG. 2B is a cross sectional view taken along the line IIB—IIB in FIG. 2A.

In FIGS. 2A and 2B, 201 is a frame for rotatably supporting the cylindrical rotating ring 102, 202 a bearing, 203 a belt, 204 a driving pulley, 205 a motor and 266 a cover for the rotating mechanism or the stand 101.

As will be seen from FIG. 2A, in the rotating mechanism for the image pickup unit according to the present embodiment, the frame 201 is installed on the floor face in upright manner which supports the cylindrical rotating ring 102 in vertical position so that the rotation center thereof assumes the rotation center axis L1 of the image pickup unit. The frame 201 is provided with an opening having substantially the same diameter as that of the cylindrical rotating ring 102. A groove is formed along the inner circumference of the frame 201. On the other hand, a groove is likely formed along the outer circumference of the cylindrical rotating ring 102, and the bearing 202 is inserted between the groove of the cylindrical rotating ring 102 inserted into the frame 201 and the groove of the frame 201 so as to permit rotation of the cylindrical rotating ring 102. Further, the motor 205 is disposed below the frame 201 and the driving pulley 204 is secured to the rotating shaft of the motor 205. The driving pulley 204 and the cylindrical rotating ring 102 are coupled by the belt 203 as illustrated in FIG. 2B, and thereby the cylindrical rotating ring 102 is designed to be rotated through rotation of the motor 205 via the driving pulley 204 and the belt 203.

Further, all of the above elements are covered by the cover member 206, and only the front face of the cylindrical rotating ring 102, in other words the end face thereof where the first and second arms 103 and 104 are disposed, is exposed from the cover member 206.

Figure 3:
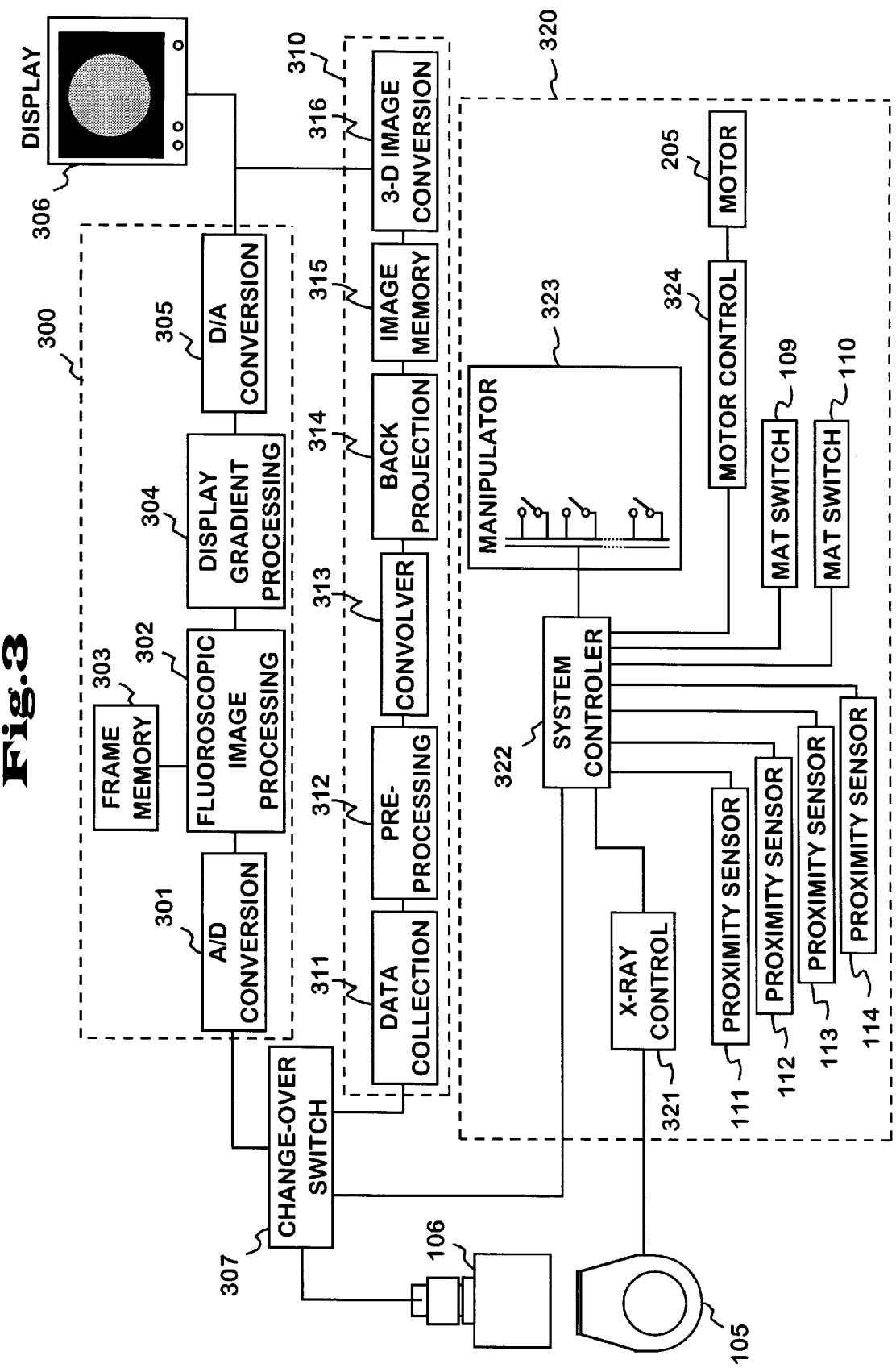
FIG. 3 is a functional block diagram of a control unit and a video image processing unit used together with the radiography apparatus as shown in FIG. 1.

FIG. 3 is a functional block diagram for explaining a structure of a control unit and an image processing unit of the radiography apparatus according to the present embodiment, wherein 300 is a radioscopic image processing unit, 310 a three dimensional image processing unit, 320 a control unit for the image pickup unit and for the radioscopic image processing unit 300 and the three dimensional image processing unit 310, 301 an A/D conversion means, 302 a fluoroscopic or radioscopic image processing means, 303 a frame memory, 304 a display gradient processing means, 305 a D/A conversion means, 306 a display means, 307 a change-over switch between the radioscopic image processing unit 300 and the three dimensional image processing unit 310, 311 a data collection means, 312 a pre-processing means, 313 a convolver, 314 a back projection means, 315 an image memory, 316 a three dimensional image conversion means, 321 an X ray control means, 322 a system controller, 323 a manipulator, and 324 a motor control means. In the radiography apparatus according to the present embodiment, since the structure of the radioscopic image processing unit 300 is substantially the same as that of a conventional one as disclosed, for example, in JP-A-7-313498(1995), an explanation thereof is omitted, and the functions and operations of the three dimensional image processing unit 310 and the control unit 320 are primarily explained hereinbelow.

In FIG. 3, the change-over switch 307 is a conventional change-over switch which changes-over analogue signals, in that analogue X ray image data outputted from the X ray detector 106 either to the fluoroscopic or radioscopic image processing unit 300 or to the three dimensional image processing unit 310 depending on a change-over control signal outputted from the system controller 322, and is constituted, for example, by a well known analogue switch. In the radiography apparatus according to the present embodiment the change-over control signal from the system controller 322 is determined based on a command signal such as radioscopic image production, X ray image production, tomographic image production and three dimensional image production inputted from the manipulator 323.

The data collection means 311 is constituted by a well known A/D conversion means which converts analogue signals into digital signals and a memory means which collects X ray image data converted into digital signals (which are hereinafter called as projection data), in that which successively converts the X ray image data obtained when rotating the image pickup unit around the patient by 360° into digital signals, in that projection data, and stores the same. The data collection means 311 is, for example, realized by an A/D converter included in a well known information processing unit for realizing the control and image processing for the radiography apparatus according to the present embodiment, a main memory in the information processing unit or an external memory device such as a magnetic disc device and a storage control program operable on the information processing unit for successively storing the A/D converted X ray image data in the memory means.

The processing means 312 is a well known preprocessing means which performs processings such as gain correction, offset correction, gamma correction, image distortion correction, logarithmic conversion and uneven sensitivity correction for the projection data collected by the data collection means 311, and, for example, is realized by a program which is operable on the information processing unit constituting the radiography apparatus according to the present embodiment.

The convolver 313 is a well known accumulating means which corrects blurring of the projection data by accumulating a preset weight function such as Sheep and Logan for the projection data after the processing, and, for example, is realized by a program which is operable on the information processing unit constituting the radiography apparatus according to the present embodiment.

The back projection means 314 is also a well known back projection means which produces an X ray absorption coefficient distribution image of an image taking region called as a CT image or tomographic image and a three dimensional image by back projecting the projection data after correcting blurring by successively adding inputted values, and, for example, is realized by a program which is operable on the information processing unit constituting the radiography apparatus according to the present embodiment.

In the present embodiment as has been explained hitherto, with the convolver 313 and the back projection means 314 reconstruction processings for reconstructing a CT image or a tomographic image and three dimensional image of an image taking region are performed. For example, for the reconstruction processing of the CT image or the tomographic image such as an image reconstruction processing method called as convolution method is used, and for the reconstruction processing of the three dimensional image such as a cone beam reconstruction processing method as disclosed in L. A. Feldkamp et al. "Practical cone beam algorism" (J. Opt. Soc. Am. A. Vol. 1, No.6, pp.612–619, 1984) is used. Further, in the present embodiment, it can be selected based on a command inputted from the manipulator 323 whether a three dimensional like X ray image is to be reconstructed or a CT image or a tomographic image is to be reconstructed as well as it is also possible to select reconstruction of both X ray images and to display the same on a common display or respective display or to produce the same.

The image memory 315 is a well known memory which stores the CT images or the tomographic images and the three dimensional images, and, for example, is realized by a program which is operable on the information processing unit constituting the radiography apparatus according to the present embodiment.

The three dimensional image conversion means 316 is constituted by a well known three dimensional like X ray image producing means which performs such as a well known volume rendering processing or maximum value projection processing for converting a three dimensional image reconstructed through the reconstruction processing into a three dimensional like absorption distribution image, and a well known level conversion means which converts X ray absorption coefficient distribution data of the CT image or the tomographic image and the three dimensional like absorption distribution image into a graphic or video image of variable density level which can be visually discriminated, and, for example, is realized by a program which is operable on the information processing unit constituting the radiography apparatus according to the present embodiment.

The system controller 322 controls the display•image production mode of the radioscopic image•CT image (tomographic image)•three dimensional like image of the X ray image data taken by the X ray detector 106 through control of the change-over switch 307 depending on a command inputted from the manipulator 323 as well as controls the operation of the image pickup unit, namely an angular position of an X ray image taken by the X ray detector 106 through control of the motor control means 324. Further, the system controller 322 judges permission or prohibition of the rotating operation of the cylindrical rotating ring 102 based on a detected output from the mat switches 109 and 110 and the proximity sensors 111, 112, 113 and 114.

Now, an operation during radioscopic image display and production mode, for instance during X ray examination of a circulatory organ, in the radiography apparatus of the present embodiment as shown in FIGS. 1, 2a and 2B, is explained with reference to FIG. 3.

At first the system controller 322 commands an operation for the motor control means 324 based on a motor rotation command inputted from the manipulator 323. The motor control means 324 which has received the operation command from the system controller 322 drives the motor 205 and sets the image pickup unit including the X ray tube 105 and the X ray detector 106 at a commanded angle.

When a projection start is commanded from the manipulator 323, the system controller 322 commands the X ray controller 321 to drive the X ray tube 105 as well as to change-over the output from the X ray detector 106 toward the radioscopic image processing unit 300 through control of the change-over switch 307.

X rays irradiated from the X ray tube 105 pass through the not illustrated patient laid on the top board 108 and are detected or image-taken by the X ray detector 106 as two dimensional X ray image data. The two dimensional X ray image data detected by the X ray detector 106 are output via the change-over switch 307 as analogue electrical signals, and are converted into digital two dimensional X ray image data, in that projection data by the A/D conversion means 301. The projection data are successively stored in the frame memory 303 connected to the fluoroscopic image processing means 302. When a collection of projection data corresponding to one image plane is completed, the fluoroscopic image processing means 302 successively reads projection data stored in the frame memory 303 by one image plane by one image plane, and outputs the projection data to the display gradient processing means 304 after performing image processing such as a contrast correction and gamma characteristic conversion on the read projection data. The display gradient processing means 304 performs a well known gradient correction for the inputted projection data and outputs the same to the D/A conversion means 305, and the D/A conversion means 305 converts the input signals into video signals in a form of analogue electrical signals, thereafter, the video signals are displayed on the image screen of the display 306 as a two dimensional projection image. Through successive execution of the above explained operations, projection images at respective moments are displayed.

When the command from the manipulator 323 is set at the image taking mode, the projection data outputted from the display gradient processing means 304 are stored in an external memory device such as a magnetic disk device and photo-magnetic disk device (not shown) connected to the information processing device included in the radiography apparatus of the present embodiment to complete the image taking operation.

Figure 4:
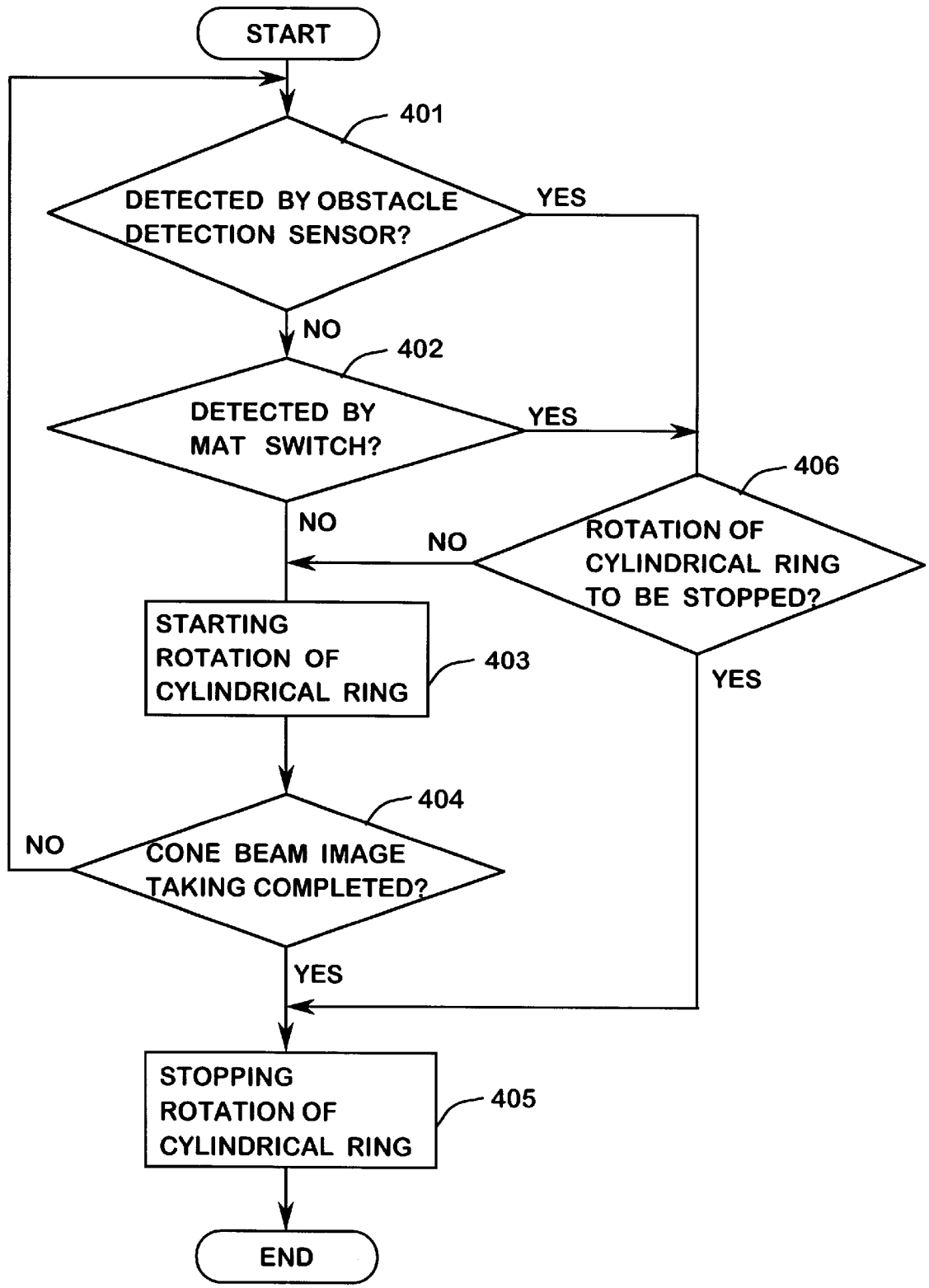
FIG. 4 is a flow chart for explaining the steps performed for a rotation movement control of an image pickup unit in the radiography apparatus as shown in FIG. 1.

Now, an operation when a three dimensional X ray image and tomographic image are taken, in other words an image taking operation through rotation with the radiography apparatus of the present embodiment, is explained with reference to FIG. 4 which shows an operation flow for explaining an operation of the radiography apparatus of the present embodiment when the image pickup unit thereof is rotated.

The present operation flow is started in response to an image taking command from the manipulator 323, and then at step 401 the system controller 322 judges whether or not the proximity sensors 111, 112, 113 and 114 detect an obstacle based on the outputs therefrom, namely judges existence and non-existence of the physician and/or operation tools within the rotating area of the image pickup unit, when it is judged that no obstacles exist through the proximity sensors 111, 112, 113 and 114 at step 401, the system controller 322 judges whether or not the mat switches 109 and 110 detect any obstacles at step 402 judges whether such as the physician enters within the rotating area of the image pickup unit. When it is judged at step 402 that no obstacles exist through the mat switches 109 and 110, the system controller 322 for the first time controls the change-over switch 307 and changes-over the output from the X ray detector 106 to the data collecting means 311. Thereafter, system controller 322 commands to the motor control means 324 to rotate the motor 205 as well as commands to the X ray control means 321 to drive the X ray tube 105. In response to this command the X ray control means 321 supplies a driving current to the X ray tube 105 to irradiate X rays in a radial shape to the patient. On the other hand, the motor control means 324 supplies a current to the motor 205 to rotate the same, thereby, a rotational driving force is transmitted to the cylindrical rotating ring 102 via the belt to rotate the image pickup unit around the patient. Thereby, the data collecting means 311 to which the X ray image data from the X ray detector 106 are inputted can collect or image-take the projection data of the patient taken while using the rotation center axis L1 as the rotation center, converting the X ray image data at every predetermined rotation angle, for example 2°~3° into projection data and storing the same into a storage means. When completion of image taking operation with the cone shaped beams is commanded after completing image taking operation amounting one corresponding to one rotation of the image pickup unit at step 404, the system controller 322 controls the motor control means 324 to stop the rotation of the motor 205 at step 405 and the routine of the present operation flow ends, in that collection of the projection data from the entire circumferential directions of the patient is ended.

On the other hand, when it is judged at steps 401 and 402 that there exists an obstacle, a judgement is required for the physician at step 406 whether the rotation of the cylindrical rotating ring 102 be stopped, and when the answer is yes, the process advances to step 405 and wherein the rotation of the cylindrical rotating ring 102 is stopped, and when the answer is no the process advances to step 403 and wherein the rotation of the cylindrical rotating ring 102 is started.

The projection data stored in the memory means included in the data collection means 311 are subjected to preprocessings such as gain correction, offset correction, gamma correction, graphic or video image distortion correction, logarithmic conversion and uneven density correction in the preprocessing means 312, and thereafter the preprocessed projection data are outputted to the convolver 313. The preprocessed projection data are then subjected to blurring correction at the convolver 313, thereafter, the blurring corrected projection data are subjected to a back projection processing at the back projection means 314 to produce a CT image, in other words tomographic image or a three dimensional like image at the image memory 315. The three dimensional like image is subjected to such as a volume rendering processing or a maximum value projection processing so as to convert the same into a three dimensional like absorption image of a plane image by the three dimensional X ray image production means in the three dimensional image conversion means 316, and thereafter the X ray absorption coefficient distribution data are converted into an image having density levels which is visibly discriminated by the level conversion means, and then the image is displayed on the display screen of the display 306 as a three dimensional like X ray image.

In the radiography apparatus according to the present embodiment as has been explained above, the cylindrical rotating ring 102 is provided having a diameter which permits insertion of the patient laid on the top board 108 along its body axis into the cylindrical space thereof which corresponds to an intermediate portion between the first and second arms 103 and 104 positioning the X ray tube 105 and the X ray detector 106 in opposing manner, namely to a portion assuming the rotation center axis thereof when the image pickup unit including the X ray tube 105 and the X ray detector 106 is rotated circumferentially around the patient, and at each end of the first and second arms 103 and 104 extending from the cylindrical rotating ring 102 the X ray tube 105 and the X ray detector 106 are disposed, namely, without prolonging the distance from the cylindrical rotating ring 102 serving as the supporting points of the respective cantilevers to the respective top ends of the arms, the image pickup unit can be rotated to any position around the patient to take X ray images, therefore the safety of the physician is enhanced. Further, the size of the entire radiography apparatus is reduced, the apparatus can be installed even in a narrow installation area.

Further, in the radiography apparatus of the present embodiment through the movement of the top board on which the patient is laid in the direction of the rotation center axis L1, in that in X axis direction, the rotary image taking of the portion from the head to foot of the patient can be performed without resetting position of the patient, for example, when the portion of the rotary image taking is for the foot portion of the patient, the top board 108 is moved in the direction of −X axis, namely the patient is moved so that the region from the chest to the abdomen of the patient enters into the cylindrical rotating ring 102. Resultantly, in the radiography apparatus of the present embodiment any portion from the head to foot of the patient can be selected for the rotary image taking without prolonging the length of the arms supporting the X ray tube 105 and the X ray detector 106. Accordingly, with the radiography apparatus of the present embodiment a three dimensional like X ray image of any image taking portion can be obtained from the X ray images around the circumference of the patient in 360° produced by the three dimensional image processing unit 310 through a well known reconstruction arithmetic operation. As a result, for example even during an IVR a three dimensional like X ray image of the patient can be obtained without moving the patient simply by temporarily resting or interrupting the IVR.

In the radiography apparatus of the present embodiment, the X ray tube 105 and the X ray detector 106 are projected outside and exposed from the external cover 206 of the cylindrical rotating ring 102, and are merely supported respectively by the first arm 103 and the second arm 104 having a simple structure and constituting a supporting member. Therefore, a large space is obtained for the physician to perform such as operation for the patient as well as the physician can quickly respond to a sudden condition change of the patient since the physician can easily observe the patient without being disturbed of his visual field.

Further, according to the radiography apparatus of the present embodiment, the X ray tube 105 and the X ray detector 106 are constituted to be separately supported in a manner of cantilever by the short first arm 103 and by the short second arm 104 which are respectively supported by the cylindrical rotating ring 102 having a comparatively small diameter, therefore, a possible offsetting of the rotation center axis of the image pickup unit caused in association with the rotation thereof is reduced. As a result, an image correction due to the offsetting is mostly unnecessitated.

FIG. 5 is a view for explaining an outline structure of another embodiment of a radiography apparatus according to the present invention in which 501 shows a stand for an image pickup unit supporting and rotating mechanism. As seen from FIG. 5, the stand 501 is movably or immovably supported not on the floor of the examination and operation room but on the ceiling or the side wall of the room while supporting the image pickup unit. However, since other structures of the present embodiment are substantially the same as those of the previous embodiment, only the structure of the stand 501 is explained hereinbelow.

One side of the stand 501 is secured either on a ceiling face of the examination and operation room, on a rail secured on the ceiling or on a rail secured on a side wall of the room. Further, the stand 501 is provided with the cylindrical rotating ring 102 having a diameter permitting insertion of the patient laid on the top board 108 in the direction of its body axis and assuming a coaxial relation with the rotation center axis when the image pickup unit including the X ray tube 105 and the X ray detector 106 is rotated around the circumference of the patient, and at each free end of the first and second arms 103 and 104 extending from the cylindrical rotating ring 102 the X ray tube 105 and the X ray detector 106 are respectively mounted.

Accordingly, through the movement of the top board 108 on which the patient is laid in the direction of the rotation center axis L1, in that in X axis direction, the rotary image taking of the portion from the head to foot of the patient can be performed without resetting position of the patient, for example, when the portion of the rotary image taking is for the foot portion of the patient, the top board 108 is moved in the direction of −X axis, namely the patient is moved so that the region from the chest to the abdomen of the patient enters into the cylindrical rotating ring 102. Resultantly, in the radiography apparatus of the present embodiment like the previous embodiment, any portion from the head to foot of the patient can be selected for the rotary image taking without prolonging the length of the arms supporting the X ray tube 105 and the X ray detector 106. Accordingly, in addition to the advantages obtained by the previous embodiment, with the present embodiment, when performing examination and operation such as an IVR with no rotation of the first and second arms 103 and 104, the space under the stand 501 can be used which further enhances working efficiency for the physician.

In the above two embodiments, the rotation angle of the image pickup unit is limited up to 360°. However, the rotation angle of the image pickup unit according to the present invention is not limited to such angle, for example, by making use of a handling mechanism of a power cable for an X ray tube and of a signal cable for an X ray detector in a well known X ray CT apparatus, the rotation angle of the image pickup unit can be extended more than 360°. In such instance when, the patient laid on the top board is moved in the direction of rotation center axis in synchronism with the rotation of the image pickup unit, an X ray image production called as volume scan can be achieved.

Further, in the above two embodiments, the cylindrical rotating ring 102 directly supports the first and second arms 103 and 104 at each free end of which the X ray tube 105 and the X ray detector 106 are respectively mounted. However, the structure of such supporting member is not limited to that of the embodiments. For example, in order to vary radiation angle of X rays with respect to the patient in a XZ plane including the body axis, the supporting member can be structured in such a manner that a third arm which slidably supports a C arm at one end of which an X ray tube is mounted and at the other end of which an X ray detector is mounted is introduced and the other end of the third arm is secured to a cylindrical rotating ring, namely, the C arm is supported to the cylindrical rotating ring via the third arm.

Although the present invention made by the present inventors is explained specifically with reference to the embodiments, however, the present invention is not limited to such embodiments and can be modified and varied in a variety of manners to an extent not to exceed the gist of the present invention.

What is claimed is:

1. A radiography apparatus comprising an image pickup unit including an X ray source for irradiating cone shaped X ray beam to a patient under examination and an image receptor disposed opposite said X ray source for receiving X ray image data of the patient by the irradiated cone shaped X ray beam;
   a cylindrical ring which carries said image pickup unit, defines a sufficient space to receive the patient therein so as to permit relative positional change of the patient with respect to said image pickup unit and is supported so as to permit rotation around its center axis;
   a first arm which extends from said cylindrical ring along its center axis and supports said X ray source in said image pickup unit;
   a second arm which extends from said cylindrical ring along its center axis so as to oppose said first arm and supports said image receptor in said image pickup unit;
   an image pickup unit rotating mechanism which causes to rotate said cylindrical ring at least one rotation so as to permit rotation of said image pickup unit one time around the patient;
   a first video image processing unit which produces a radioscopic video image based on the X ray image data obtained from said image pickup unit;
   a second video image processing unit which reconstructs a three dimensional video image based on the X ray image data obtained from said image pickup unit; and
   a change-over device which changes-over the X ray image data obtained from said image pickup unit either to said first video image processing unit or to said second video image processing unit.

2. A radiography apparatus according to claim 1, further comprising:
   an obstacle detector unit disposed at said image pickup unit, said first arm and/or said second arm for detecting existence and non-existence of a possible obstacle in a rotating range of said image pickup unit which rotates in association with rotation of said cylindrical ring; and
   a cylindrical ring rotation control unit which causes to stop the rotation of said cylindrical ring by said image pickup unit rotating mechanism when said obstacle detector unit detects existence of an obstacle in the rotating range of said image pickup unit.

3. A radiography apparatus according to claim 2, wherein said obstacle detector unit includes a plurality of proximity sensors, and said plurality of proximity sensors are arranged on said image pickup unit, said first arm and/or said second arm along the body axis of the patient without overlapping each other.

4. A radiography apparatus comprising:
   an image pickup unit including an X ray source for irradiating cone shaped X ray beam to a patient under examination and an image receptor disposed opposite the X ray source for receiving X ray image data of the patient by the irradiated cone shaped X ray beam;
   a supporting member which carries said image pickup unit;
   a rotary member which carries said supporting member, defines a sufficient space to receive the patient therein so as to permit relative positional change of the patient with respect to said image pickup unit and is supported so as to permit rotation around its center axis;
   an image pickup unit rotating mechanism which causes to rotate said rotary member at least one rotation so as to permit rotation of said image pickup unit one time around the patient;
   a video image processing and control unit which processes and controls the X ray image data obtained from said image pickup unit; and
   an external member which covers said rotary member and said image pickup unit rotating mechanism other than said image pickup unit and said supporting member carrying said image pickup unit, whereby said image pickup unit and said supporting member carrying said image pickup unit are exposed outside said external covering member.

5. A radiography apparatus according to claim 4, wherein said supporting member includes:
   a first arm which extends from said rotary member along its center axis and supports said X ray source in said image pickup unit; and
   a second arm which extends from said rotary member along its center axis while opposing to said first arm and supports said X ray receptor in said image pickup unit.

6. A radiography apparatus according to claim 4, wherein said supporting member includes:
   a C arm which carries at respective ends said X ray source and said X ray receptor in said image pickup unit; and
   an arm which slidably supports said C arm and is carried by said rotary member.

7. A radiography apparatus according to claim 4, wherein said video image processing and control unit includes:
   a first image processing unit which produces a radioscopic video image based on the X ray image data obtained from said image pickup unit;
   a second video image processing unit which reconstructs a three dimensional video image based on the X ray image data obtained from said image pickup unit; and
   a change-over device which changes-over the X ray image data obtained from said image pickup unit either to said first video image processing unit or to said second video image processing unit.

8. A radiography apparatus comprising:
   an image pickup unit including an X ray source for irradiating cone shaped X ray beam to a patient under examination and an image receptor disposed opposite said X ray source for receiving X ray image data of the patient by the irradiated cone shaped X ray beam;
   a cylindrical ring which carries said image pickup unit, defines a sufficient space to receive the patient therein so as to permit relative positional change of the patient with respect to said image pickup unit and is supported so as to permit rotation around its center axis;
   a first arm which extends from said cylindrical ring along its center axis and supports said X ray source in said image pickup unit;
   a second arm which extends from said cylindrical ring along its center axis so as to oppose said first arm and supports said image receptor in said image pickup unit;
   an image pickup unit rotating mechanism which causes to rotate said cylindrical ring at least one rotation so as to permit rotation of said image pickup unit one time around the patient;

a first video image processing unit which produces a radioscopic video image based on the X ray image data obtained from said image pickup unit;

a second video image processing unit which reconstructs a three dimensional video image based on the X ray image data obtained from said image pickup unit;

a change-over device which changes-over the X ray image data obtained from said image pickup unit either to said first video image processing unit or to said second video image processing unit;

a display unit which displays at least one of the radioscopic video image from said first video image processing unit and the three dimensional video image from said second video image processing unit; and an external member which covers said cylindrical ring and said image pickup unit rotating mechanism other than said image pickup unit and said first and second arms carrying said image pickup unit, whereby said image pickup unit and said first and second arms carrying said image pickup unit are exposed outside said external covering member.

9. A radiography apparatus according to claim 8, wherein said image pickup unit rotating mechanism is mounted on a floor of an examination and operation room.

10. A radiography apparatus according to claim 8, wherein said image pickup unit rotating mechanism is mounted on either a ceiling or on a side wall other than a floor of an examination and operation room.

11. A radiography apparatus comprising:

an image pickup unit including an X ray source for irradiating cone shaped X ray beam to a patient under examination and an image receptor disposed opposite the X ray source for receiving X ray image data of the patient by the irradiated cone shaped X ray beam;

a supporting member which carries said image pickup unit;

a rotary member which carries said supporting member, defines a sufficient space to receive the patient therein so as to permit relative positional change of the patient with respect to said image pickup unit and is supported so as to permit rotation around its center axis;

an image pickup unit rotating mechanism which causes to rotate said rotary member at least one rotation so as to permit rotation of said image pickup unit one time around the patient;

a video image processing unit which processes the X ray image data obtained from said image pickup unit;

a display unit which displays an X ray image processed in said video image processing unit; and an external member which covers said rotary member and said image pickup unit rotating mechanism other than said image pickup unit and said supporting member carrying said image pickup unit, whereby said image pickup unit and said supporting member carrying said image pickup unit are exposed outside said external covering member.

12. A radiography apparatus according to claim 11, wherein said display unit displays at least one of a radioscopic video image and a three dimensional video image based on the X ray image data obtained from said image pickup unit and processed in said video image processing unit.

13. A radiography apparatus according to claim 11, wherein said video image processing unit includes:

a first image processing unit which produces a radioscopic video image based on the X ray image data obtained from said image pickup unit;

a second video image processing unit which reconstructs a three dimensional video image based on the X ray image data obtained from said image pickup unit; and a change-over device which changes-over the X ray image data obtained from said image pickup unit either to said first video image processing unit or to said second video image processing unit.

* * * * *